United States Patent
Stein

[11] 4,022,213
[45] May 10, 1977

[54] DRIP URINAL

[76] Inventor: David Stein, 16740 NE. 9 Ave. No. 508, N. Miami Beach, Fla. 33162

[22] Filed: Aug. 21, 1975

[21] Appl. No.: 606,551

[52] U.S. Cl. .............................................. 128/295
[51] Int. Cl.² ........................................ A61F 5/44
[58] Field of Search ................... 128/275, 295, 283

[56] References Cited
UNITED STATES PATENTS

| | | | |
|---|---|---|---|
| 919,875 | 4/1909 | Johnson | 128/294 |
| 1,490,793 | 4/1924 | Ajamian et al. | 128/295 |
| 3,161,198 | 12/1964 | Moxley | 128/295 |
| 3,526,227 | 9/1970 | Appelbaum | 128/295 |

Primary Examiner—G.E. McNeill
Assistant Examiner—Wenceslao J. Contreras
Attorney, Agent, or Firm—Jack D. Slobod

[57] ABSTRACT

A urinal worn about the male organ includes a tubular sleeve having a mouth at one end for receiving the male organ and a hose fitting outlet at the other end. A conical resilient tubular sheath is secured to the sleeve along the mouth and extends into the tube for sealing about the tip of the male organ, and a resilient apertured sheet extending across the mouth of the sleeve seals about the base of the male organ. A support garment is provided having snap fasteners mutually engageable with snap fasteners carried longitudinally projecting from an annular ring forming the mouth of the sleeve.

1 Claim, 3 Drawing Figures

DRIP URINAL

FIELD OF THE INVENTION

The present invention relates generally to urinals adapted to be worn covering the male organ for directing urine to an outlet orifice for connection to a urine collection bag. In its particular aspects the present invention relates to a urinal adapted to seal both against the end and the base of the male organ to prevent back flow of urine onto the clothing.

BACKGROUND OF THE INVENTION

Various urinals have heretofore been provided in the form of a tubular sleeve provided with a thin rubber sheath adapted to be stretched over the penis for sealing purposes. Such sheaths, because of difficulty in stretching over the penis, would generally tear apart after only about one week of use resulting in wetting of the clothing. U.S. Pat. No. 3,526,227 to Applebaum is illustrative of the prior devices.

OBJECTS OF THE INVENTION

It is an object of the present invention to provide a urinal having durable and comfortable means for sealing against the male organ.

It is a further object of the present invention to provide a urinal for a male organ which is configured to prevent wetting of the clothing.

SUMMARY OF THE INVENTION

Briefly, the aforementioned and other objects of the present invention are satisfied by providing an apertured resilient sheet across the mouth of a urinal sleeve for sealing comfortably about the base of the penis. The provision of this sheet or diaphragm extending radially inward from the mouth of a urinal sleeve, provides a backup seal, when the usual inner sheath should tear, to prevent the clothing from being wetted. The sheet is carried by an annular ring forming the mouth of the urinal sleeve.

I further provide a support garment for the sleeve which has an aperture through which the penis is inserted. Snap fasteners angularly spaced about the aperture and about the annular ring enable a longitudinal mounting of the sleeve to the support garment.

Other objects, features and advantages of the present invention will become apparent upon perusal of the following detailed description of the preferred embodiment thereof when taken in conjunction with the appended drawing wherein.

DETAILED DESCRIPTION

Figure 1:
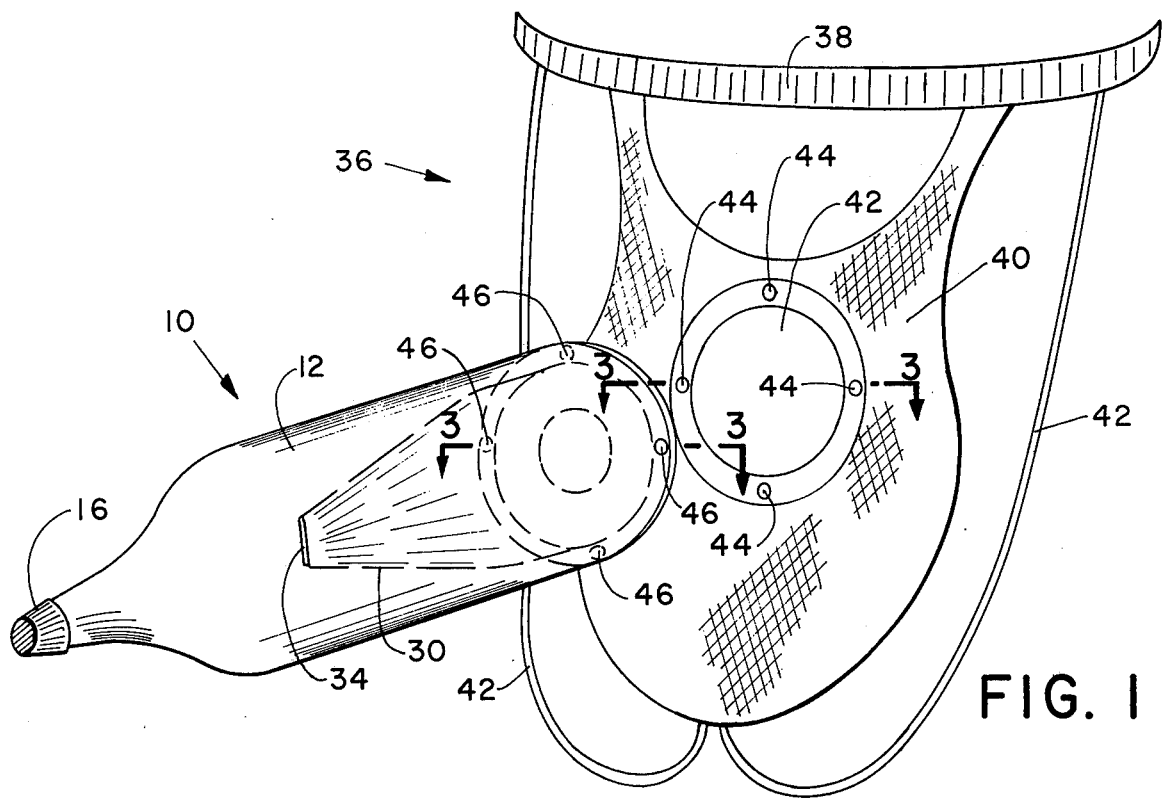
FIG. 1 is a pictorial exploded view of the drip urinal and support garment therefor of the present invention.
Figure 3:
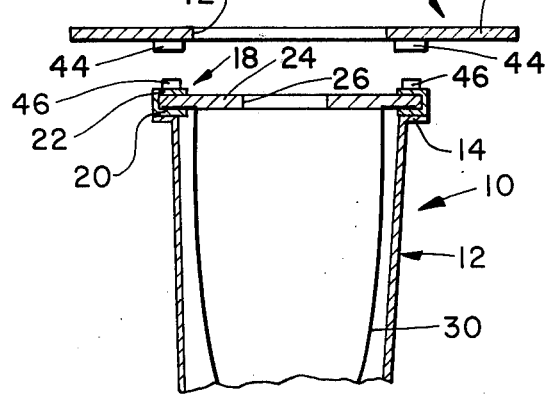
FIG. 3 is a cross-sectional view of the drip urinal and garment in the plane indicated by the lines 3—3 in FIG. 1.
Figure 2:
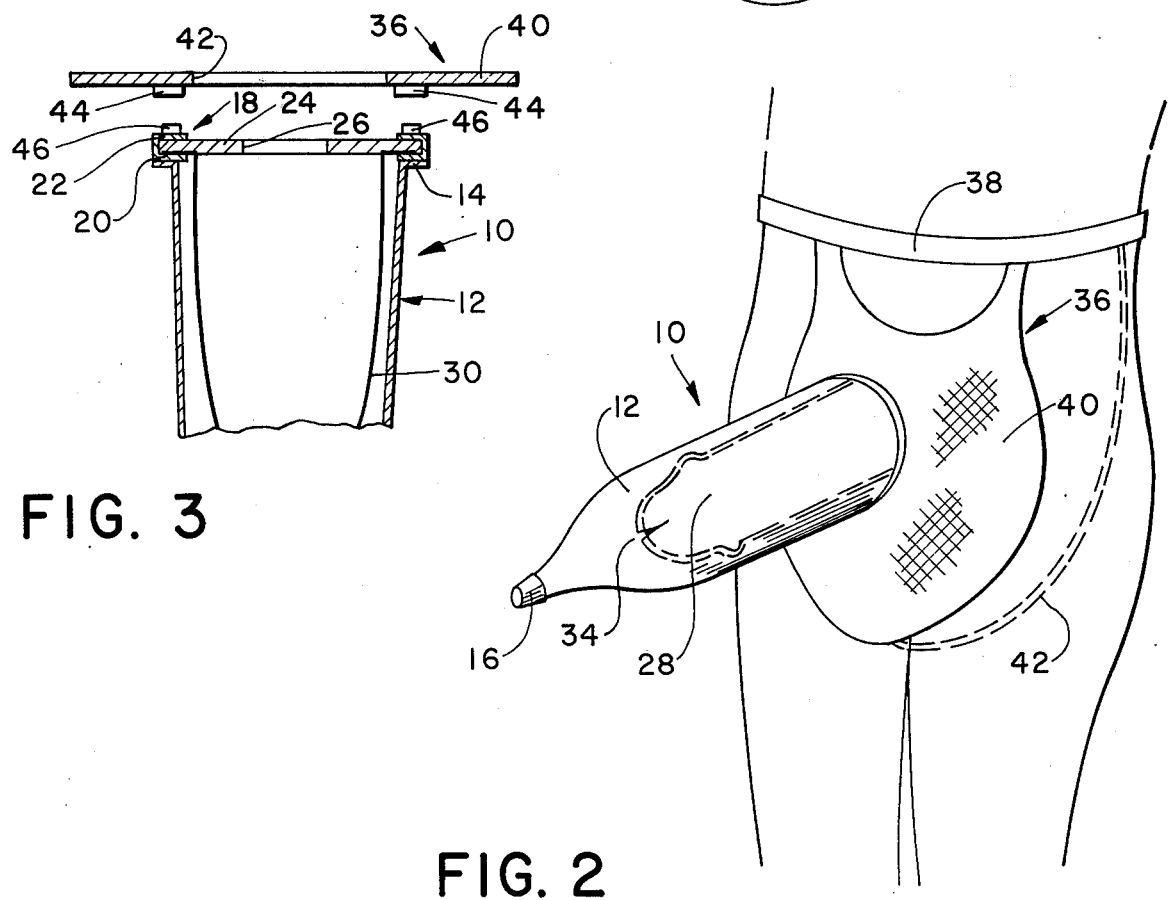
FIG. 2 is a pictorial presentation similar to FIG. 1 but showing the drip urinal and support garment as worn.

Referring to FIGS. 1 through 3 of the drawing, the drip urinal 10 of the present invention comprises a bottle-shaped tubular sleeve 12 having an open mouth at a radially outwardly directed flange 14 at one end of the sleeve. The other end of sleeve 12 converges in cross-section to define an outlet hose fitting 16 for conveying urine to a collection bag (not shown).

An annular ring 18 of "U"-shaped cross-section includes a pair of longitudinally spaced, radially inwardly directed flanges 20 and 22. Flanges 20 and 14 are adhesively secured together.

Between flanges 20 and 22, the circular periphery of a rubber disc 24 is captured. The disc 24 comprises a rubber sheet of approximately one-eighth inch in thickness which has a central hole 26 of approximately seven-eighths of an inch in diameter for sealably engaging the base of the penis 28. By extending radially inwardly across the mouth of sleeve 12, the disc or sheet 24 functions as a diaphragm sealing against the penis 28 preventing the back up of urine through the mouth of sleeve 12 and onto the clothing. The sheet 24, being of one-eighth inch thickness is quite durable and is not subject to tearing.

I further provide a resilient rubber conical tubular sheath 30, within sleeve 12, which is sufficiently thin to be stretched over the penis 28. Sheath 30, as is usual, is open at both ends. A radially outwardly directed flange 32 at the large diameter end of sheath 30 is sandwiched between flange 20 and disc 24 to secure the sheath along the mouth of sleeve 12. Sheath 30 extends part way along the length of sleeve 12 and the small diameter end of the sheath sealably engages the tip of penis 28, also insuring against the back-up of urine by directing urine into sleeve 12 through the opening 34 in the end of the sheath.

Although the sheath 30, like all such sheaths is subject to tearing, the sheet 24 provides an adequate seal by itself to prevent urine backup onto the clothing.

For mounting the urinal 10 on the body, I provide a rubber garment 36 including a waistband 38, a sheet 40 suspended from the waistband and a pair of thigh straps 42 running between the lower portion of sheet 40 and the waistband 38. The sheet 40 is adapted to overly the genital area. A hole 42 in sheet 40 is provided to enable the penis to be passed through the sheet and into the urinal 10. To enable mounting the urinal to garment 36 over hole 42, a plurality of female snap fasteners 44 are spaced angularly about hole 42 and mate with male fasteners 46 provecting longitudinally from flange 22 of ring 18.

While the preferred embodiment of the present invention has been described in specific detail, it should be noted that numerous modifications, additions and omissions in the details thereof are possible within the spirit and scope of the invention claimed herein.

What is claimed is:

1. A urinal adapted to be worn over the male organ comprising: an elongated tubular sleeve having a mouth at one end for receiving the male organ and having an outlet means on the other end, a tubular resilient open-ended sheath secured to said sleeve along said mouth and extending into said sleeve, a resilient centrally apertured planar disc carried by the mouth of said sleeve, said disc extending radially inward from said mouth for sealing engagement about the male organ, a support garment having an aperture for receiving the male organ, and mutually engageable snap fastener means projecting from said support garment about said aperture and from said mouth for longitudinal engagement of said sleeve to said garment.

* * * * *